US010046180B2

(12) United States Patent
Tolo

(10) Patent No.: US 10,046,180 B2
(45) Date of Patent: Aug. 14, 2018

(54) REDUCED HEATING IN OVERLAPPING NEAR FIELD REGIONS OF HIGH INTENSITY FOCUSED ULTRASOUND

(71) Applicant: Profound Medical Inc., Mississauga (CA)

(72) Inventor: Jaakko Juhani Tolo, Eindhoven (NL)

(73) Assignee: Profound Medical Inc., Mississauga, ON (CA)

( * ) Notice: Subject to any disclaimer, the term of this patent is extended or adjusted under 35 U.S.C. 154(b) by 8 days.

(21) Appl. No.: 14/431,932

(22) PCT Filed: Sep. 25, 2013

(86) PCT No.: PCT/IB2013/058837
§ 371 (c)(1),
(2) Date: Mar. 27, 2015

(87) PCT Pub. No.: WO2014/053950
PCT Pub. Date: Apr. 10, 2014

(65) Prior Publication Data
US 2015/0246249 A1 Sep. 3, 2015

Related U.S. Application Data

(60) Provisional application No. 61/708,095, filed on Oct. 1, 2012.

(51) Int. Cl.
*A61H 1/00* (2006.01)
*A61N 7/02* (2006.01)
(Continued)

(52) U.S. Cl.
CPC .......... *A61N 7/02* (2013.01); *A61B 2090/374* (2016.02); *A61N 2007/0056* (2013.01);
(Continued)

(58) Field of Classification Search
CPC .................................. A61N 7/02; A61N 7/00
See application file for complete search history.

(56) References Cited

U.S. PATENT DOCUMENTS 5,520,188 A 5/1996 Hennige
7,766,833 B2 8/2010 Lee
(Continued)

FOREIGN PATENT DOCUMENTS

WO 200243804 A1 6/2002
WO 2004103472 A1 12/2004
(Continued)

*Primary Examiner* — Hien Nguyen
(74) *Attorney, Agent, or Firm* — Intrinsic Law Corp.

(57) ABSTRACT

The invention provides for a medical apparatus (200, 400, 500) comprising a high intensity focused ultrasound system (206). Machine executable instructions (260, 262, 264, 266, 408, 526) in a memory (250) cause a processor (244) to: receive (100) location data (252) descriptive of multiple sonication points (224, 226, 228, 230); determine (102) a sonication path (254) for each of the multiple sonication points using a geometric transducer element model (262); detect (104) an overlap region (256, 306) using the sonication path in the near field region; determine (106) transducer control commands (258) using the overlap region, wherein the transducer commands are operable to control the multiple transducer elements to reduce the deposition of ultrasonic energy in the overlap region during sonication of the two or more sonication points; and control (108) the high intensity focused ultrasound system using the transducer control commands.

16 Claims, 5 Drawing Sheets

(51) Int. Cl.
*A61N 7/00* (2006.01)
*A61B 90/00* (2016.01)

(52) U.S. Cl.
CPC ................ *A61N 2007/0078* (2013.01); *A61N 2007/0095* (2013.01); *A61N 2007/027* (2013.01)

(56) References Cited

U.S. PATENT DOCUMENTS

| | | |
|---|---|---|
| 8,725,232 B2 | 5/2014 | Vahala et al. |
| 2006/0058671 A1* | 3/2006 | Vitek ................ A61N 7/02 600/447 |
| 2008/0039746 A1 | 2/2008 | Hissong |
| 2011/0270075 A1 | 11/2011 | Vitek |

FOREIGN PATENT DOCUMENTS

| | | |
|---|---|---|
| WO | 2006018686 A1 | 2/2006 |
| WO | 2011013001 A1 | 2/2011 |
| WO | 2011080631 A2 | 7/2011 |
| WO | 2012123894 A1 | 9/2012 |

\* cited by examiner

REDUCED HEATING IN OVERLAPPING NEAR FIELD REGIONS OF HIGH INTENSITY FOCUSED ULTRASOUND

CROSS-REFERENCE TO PRIOR APPLICATIONS

This application is the U.S. National Phase application under 35 U.S.C. § 371 of International Application No. PCT/IB2013/058837, filed on Sep. 25, 2013, which claims the benefit of U.S. Provisional Patent Application No. 61/708,095, filed on Oct. 1, 2012. These applications are hereby incorporated by reference herein.

TECHNICAL FIELD

The invention relates to magnetic resonance guided high intensity focused ultrasound, in particular to reduce the deposition of ultrasound energy in the overlapping near field regions of multiple sonication points.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to kill regions of cancer cells selectively. This technique has been applied to the treatment of uterine fibroids, and has reduced the need for hysterectomy procedures.

To selectively treat tissue, a focused ultrasonic transducer can be used to focus the ultrasound on a particular treatment or target volume. The transducer is typically mounted within a medium, such as degassed water, that is able to transmit ultrasound. Actuators are then used to adjust the position of the ultrasonic transducer and thereby adjust the tissue region that is being treated.

Focused ultrasonic transducers also typically have multiple transducer elements, wherein the amplitude and/or phase of the transducer elements are controllable. In particular the phase of individual or groups of transducer elements is often controlled to control the location of the focus of the ultrasound. This enables the rapid adjustment location of the focus and the sequential sonication of different sonication points or locations. The tissue of a subject between the transducer and a sonication point is typically referred to as the near field region. The ultrasound travels through the near field region to the sonication volume. This intermediate tissue is also heated, although not as much as the sonication volume. When sonicating multiple sonication points the near field region of the different sonication points may overlap. Because a particular portion of the near field region may overlap it may be heated multiple times. To avoid overheating this overlapping near field region there may need to be delays between sonicating multiple sonication points.

SUMMARY OF THE INVENTION

The invention provides for a medical apparatus, a computer program product, and a method. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising a high-intensity focused ultrasound system. The high-intensity focused ultrasound system comprises an ultrasound transducer with multiple transducer elements for focusing ultrasound into a sonication volume. There is a near field region between the ultrasonic transducer and the sonication volume. That is to say that the ultrasound transducer is operable for generating a near field region when focusing ultrasound into the sonication volume. A near field region as used herein encompasses a region which ultrasound passes through on its way to the sonication volume or focal point. As the ultrasound also passes through the near field region it is heated, but not nearly as much as it is inside the sonication volume. The multiple transducer elements are controllable in groups. The transducer elements may be controllable such that the phase and/or amplitude of individual transducer elements or a group of elements may be changed. For instance the phase may be used to shift the position of the focus. The amplitude of individual transducer elements or groups of transducer elements may also be changed. As such the individual transducer elements or groups of them may also be turned off completely.

The medical apparatus further comprises a memory for storing machine-executable instructions. The medical apparatus further comprises a processor for controlling the medical apparatus. Execution of the instructions causes the processor to receive location data descriptive of multiple sonication points. The location data is essentially data which describes the location of multiple sonication points. These are points which are to be sonicated by moving the sonication volume to within the sonication point. The location data could be received for example from: a treatment plan, a medical imaging system, manual input, and combinations thereof.

Execution of the instructions further cause the processor to determine a sonication path for each of the multiple sonication points using a geometric transducer element model. The sonication path is a rough approximation or approximation of the path that ultrasound will take in order to get to each of the multiple sonication points. The sonication path may be created with a simple geometric model for each of the transducer elements or groups of transducer elements or may also use a ray tracing method.

Execution of the instructions further causes the processor to detect an overlap region using the sonication path for each of the multiple sonication points. The overlap region indicates an overlap of the sonication path of two or more sonication points in the near field region. Typically the ultrasound transducer has a concave shape and the ultrasound transducer elements are aimed such that they all focus roughly into a particular sonication volume or focal point. The near field region winds up being significantly larger than the sonication volume. If sonication volumes are adjacent to each other or within a particular predetermined distance portions of the near field region can overlap. As mentioned before ultrasound traveling through the near field region has the effect of heating regions of tissue. If near field regions overlap in sonication points that are sonicated then it is possible that certain near field regions will be heated more than once. This may lead to unwanted heating of the near field region which may be hazardous to the subject.

Execution of the instructions further cause the processor to determine transducer control commands using the overlap region. The transducer control commands are operable to control the multiple transducer elements to reduce the deposition of ultrasonic energy in the overlap region during sonication of the two or more sonication points. Quite simply the amplitude and/or phase of ultrasonic power delivered to the ultrasonic transducers is modified such that the path that the ultrasound takes in the overlap region is reduced. This could include turning off individual transducer elements or a group of transducer elements or it may involve reducing the amplitude during sonication of one or more of the sonication points. There are different ways that this may be optimized.

Execution of the instructions further cause the high-intensity focused ultrasound system to sequentially sonicate the multiple sonication points using the transducer control commands. The transducer control commands cause the high-intensity focused ultrasound system to sequentially sonicate the multiple sonication points. This embodiment may have the benefit of limiting the thermal dose in the near field. This may have the benefit that the beam of ultrasound produced by the ultrasound transducer is beam-shaped. This may mean that in order to sonicate the multiple sonication points there is less of a waiting time because the overlapping regions are not heated or heated less than they would be if the invention is not practiced.

In another embodiment execution of the instructions further cause the processor to receive a current thermal property map descriptive of a thermal property in the near field region. The thermal property map could either be determined using a medical imaging technique such as thermal magnetic resonance imaging or may be created by a model which uses data from previous sonications to create the thermal property map. Execution of the instructions further cause the processor to calculate a predicted thermal property map of the thermal property using the transducer control commands and a transducer thermal model. The transducer thermal model may for instance be a thermal acoustic model which is used to predict the change in temperature caused by sonicating the multiple sonication points with the transducer control commands.

Execution of the instructions further causes the processor to determine corrected transducer control commands using the predicted thermal property map. The corrected transducer control commands are operable to control the multiple transducer elements. The instructions cause the processor to use the corrected transducer control commands to control the high-intensity focused ultrasound system during the sequential sonication of the multiple sonication points. In this embodiment the current thermal property map describes a current thermal property of the near field region. This is used to better determine the effect of the sonication of the multiple sonication points. For instance if the current thermal property map is a temperature map the corrected transducer control commands are operable to control the multiple transducer elements to limit the temperature in the near field region to a predetermined threshold. This may prevent damage to the subject in the near field region. A current thermal property map and a predicted thermal property map are both three-dimensional maps of a thermal property of a subject in the near field region.

An alternative to a temperature map the thermal property map may also be used to minimize the temperature without a threshold to make the cooling time shorter. Also the thermal dose calculated from temperature maps either measured or predicted with simulations can be used as the limiting measure instead of temperature.

In another embodiment execution of the instructions further cause the processor to receive a previous thermal dose. The previous thermal dose is descriptive of a thermal does caused by a previous sonication using the high-intensity focused ultrasound system. The current thermal property map and/or the predicated thermal property map are at least partially determined using the previous thermal dose. This embodiment may be beneficial because it may be useful in predicting the future effect of the multiple sonication points on tissue necrosis or damage within the near field region.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

MR thermometry data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-starweighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonant frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

In another embodiment the medical apparatus further comprises a magnetic resonance imaging system for acquiring thermal magnetic resonance data. Execution of the instructions further causes the processor to acquire the thermal magnetic resonance data. Execution of the instructions further cause the processor to calculate the current thermal property map at least partially using the thermal magnetic resonance data. The thermal magnetic resonance data could have been acquired during or after the previous sonication.

In another embodiment execution of the instructions further causes the processor to calculate the current thermal property map using the transducer thermal model and a set of previous transducer control commands. The thermal model and the magnetic resonance thermometry could be used in combination with the modeling in some embodiments.

In another embodiment execution of the instructions further cause the processor to repeatedly receive the location data descriptive of the multiple sonication points. Execution of the instructions further cause the processor to repeatedly determine the sonication path for each of the multiple sonication points using the geometric transducer element model. Execution of the instructions further causes the processor to repeatedly detect an overlap region using the sonication path for each of the multiple sonication points. The overlap region indicates an overlap of the sonication path of two or more sonication points in the near field region. Execution of the instructions further cause the processor to repeatedly determine the transducer control commands operable to control the multiple transducer elements to reduce the deposition of ultrasonic energy in the overlap region during sonication of the two or more sonication points. Execution of the instructions further cause the processor to repeatedly control the high-intensity focused ultrasound system to sequentially sonicate the multiple sonication points using the transducer control commands. In summary in this embodiment the actions performed by the processor are done repeatedly. This may be beneficial because there may be multiple groups of sonication points that are treated in the course of using the medical apparatus on a subject.

In another embodiment execution of the instructions further cause the processor to repeatedly receive the current thermal property map. Execution of the instructions further cause the processor to repeatedly calculate the predicted thermal property map using the transducer control commands and the transducer thermal model. Execution of the instructions further cause the processor to repeatedly determine the corrected transducer control commands using the predicted thermal property map. Execution of the instructions further cause the processor to repeatedly control the high-intensity focused ultrasound system to sequentially sonicate the multiple sonication points using the transducer control commands.

In another embodiment the multiple transducer elements are controlled to reduce the deposition of ultrasonic energy in the overlap region during sonication of the two or more sonication points using any one of the following: selectively switching off a first portion of the multiple transducer elements, selectively reducing the amplitude of ultrasonic energy generated by a second portion of the multiple transducer elements, and combinations thereof. The first and second portions of the multiple transducer elements may be one or more individual transducer elements or they may also be groups of transducer elements.

In another embodiment each of the multiple transducer elements are individually controllable.

In another embodiment the thermal properties are any one of the following: temperature, maximum temperature, thermal dose, cool down time, and combinations thereof.

In another aspect the invention provides for a computer program product comprising machine-executable instructions for execution by a processor controlling the medical apparatus. The medical apparatus comprises a high-intensity focused ultrasound system comprising an ultrasound transducer with multiple transducer elements for focusing ultrasound into a sonication volume. There is a near field region between the ultrasonic transducer and the sonication volume. The multiple transducer elements are controllable in groups. Execution of the instructions causes the processor to receive location data descriptive of the multiple sonication points. Execution of the instructions further cause the processor to determine a sonication path for each of the multiple sonication points using a geometric transducer element model. Execution of the instructions further causes the processor to detect an overlap region using the sonication path for each of the multiple sonication points. The overlap region indicates an overlap of the sonication path of two or more sonication points in the near field region.

Execution of the instructions further cause the processor to determine transducer control commands using the overlap region. The transducer control commands are operable to control the multiple transducer element to reduce the deposition of ultrasonic energy in the overlap region during sonication of the two or more sonication points. Execution of the instructions further cause the processor to control the high-intensity focused ultrasound system to sequentially sonicate the multiple sonication points using the transducer control commands. Execution of the instructions further causes the processor to receive a current thermal property map descriptive of a thermal property in the near field region.

Execution of the instructions further cause the processor to calculate a predicated thermal property map of the thermal property using the transducer control commands and a transducer thermal model. Execution of the instructions further causes the processor to determine corrected transducer control commands using the predicted thermal property map. The corrected transducer control commands are operable to control the multiple transducer elements. The instructions cause the processor to use the corrected transducer control commands to control the high-intensity focused ultrasound system during the sequential sonication of the multiple sonication points.

In another embodiment execution of the instructions further cause the processor to receive a previous thermal dose. The previous thermal dose is descriptive of the thermal dose caused by a previous sonication using a high-intensity focused ultrasound system. The current thermal property map and/or the predicted thermal property map are at least partially determined using the previous thermal dose.

In another embodiment the medical apparatus further comprises a magnetic resonance imaging system for acquiring thermal magnetic resonance data. Execution of the instructions further causes the processor to acquire the thermal magnetic resonance data. Execution of the instructions further cause the processor to calculate the current thermal property map at least partially using the thermal magnetic resonance data.

In another embodiment the medical apparatus comprises a high-intensity focused ultrasound system comprising an ultrasound transducer with multiple transducer elements for focusing ultrasound into a sonication volume. There is a near field region between the ultrasonic transducer and the sonication volume. The multiple transducer elements are controllable in groups. The method comprises the step of receiving location data descriptive of multiple sonication points. The method further comprises the step of determining a sonication path for each of the multiple sonication points using a geometric transducer element model.

The method further comprises the step of detecting an overlap region using the sonication path for each of the multiple sonication points. The overlap region indicates an overlap of the sonication path of two or more sonication points in the near field region. The method further comprises the step of determining transducer control commands using the overlap region. The transducer control commands are operable to control the multiple transducer elements to reduce the deposition of ultrasonic energy in the overlap region during sonication of the two or more sonication points. The method further comprises the step of controlling the high-intensity focused ultrasound system to sequentially sonicate the multiple sonication points using the transducer control commands.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
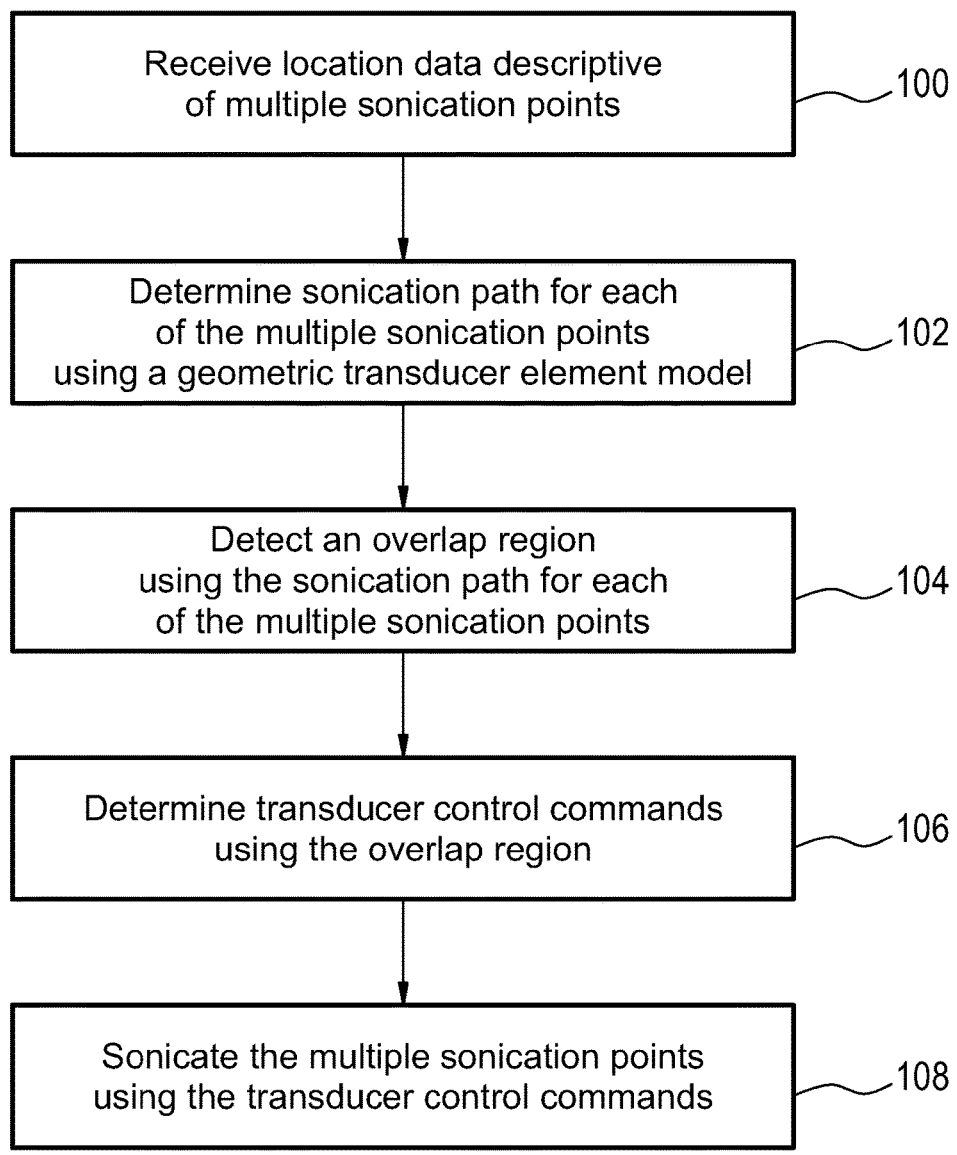
FIG. 1 shows a flow chart which illustrates an example of a method.

FIG. 1 shows a flowchart which illustrates a method according to an embodiment of the invention. In step 100 location data descriptive of multiple sonication points is received. Next in step 102 a sonication path is determined for each of the multiple sonication points using a geometric transducer element model. Next in step 104 an overlap region is detected using the sonication path for each of the multiple sonication points. The overlap region indicates an overlap of the sonication path of two or more sonication points in the near field region. In some embodiments more than one overlap region may be detected. Next in step 106 transducer control commands are determined or generated which are operable to control the multiple transducer element to reduce the deposition of ultrasonic energy in the overlap region during sonication of the two or more sonication points. And finally in step 108 the high-intensity focused ultrasound system is controlled using the transducer control commands to sequentially sonicate the multiple sonication points.

Figure 2:
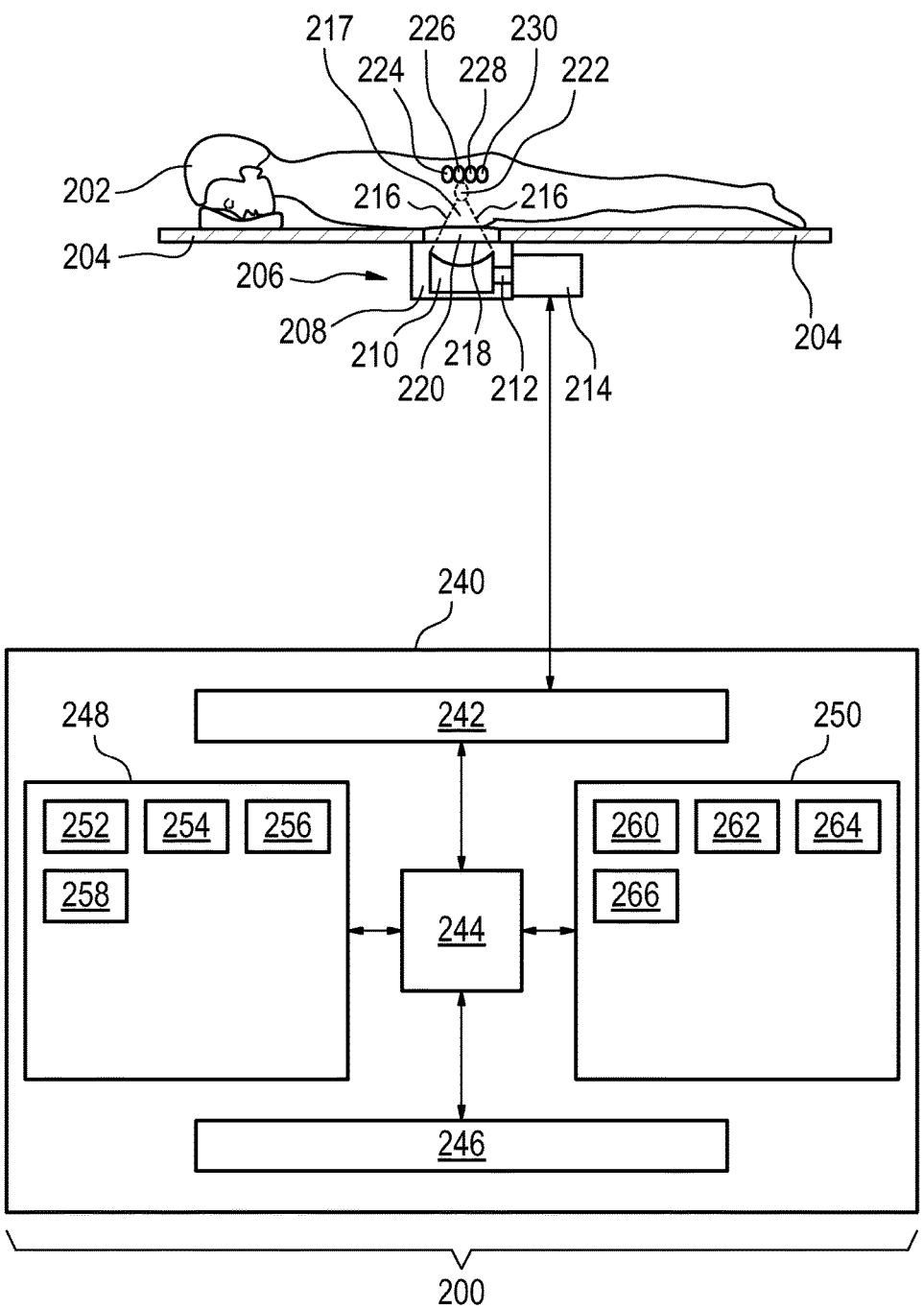
FIG. 2 shows an example of a medical apparatus.

FIG. 2 illustrates an example of a medical apparatus 200. A subject 202 is shown as reposing on a subject support 204. The medical apparatus 200 comprises a high-intensity focused ultrasound system 206. The high-intensity focused ultrasound system comprises 206 a fluid-filled chamber 208. Within the fluid-filled chamber 208 is an ultrasound transducer 210. Although it is not shown in this figure the ultrasound transducer 210 comprises multiple ultrasound transducer elements each capable of generating an individual beam of ultrasound. This may be used to steer the location of a sonication volume 222 electronically by controlling the phase and/or amplitude of alternating electrical current supplied to each of or groups of the ultrasound transducer elements. Point 222 represents the adjustable focus of the medical apparatus 200.

The ultrasound transducer 210 is connected to a mechanism 212 which allows the ultrasound transducer 210 to be repositioned mechanically. The mechanism 212 is connected to a mechanical actuator 214 which is adapted for actuating the mechanism 212. The mechanical actuator 212 also represents a power supply for supplying electrical power to the ultrasound transducer 210. In some embodiments the power supply may control the phase and/or amplitude of electrical power to individual ultrasound transducer elements.

The ultrasound transducer 210 generates ultrasound which is shown as following the path 216. The ultrasound 216 goes through the fluid-filled chamber 208 and through an ultrasound window 218. In this embodiment the ultrasound then passes through a gel pad 220. The gel pad 220 is not necessarily present in all embodiments but in this embodiment there is a recess in the subject support 204 for receiving a gel pad 220. The gel pad 220 helps couple ultrasonic power between the transducer 210 and the subject 202. After passing through the gel pad 220 the ultrasound 216 passes through a near field region 217 of the subject 202 and then is focused to a sonication volume 222 or target zone.

The sonication volume 222 may be moved through a combination of mechanically positioning the ultrasonic transducer 210 and electronically steering the position of the sonication volume 222.

Located within the subject 204 there are four sonication points 224, 226, 228, 230 which are visible. The sonication volume 222 may be moved onto each of the sonication points 224, 226, 228, 230 by a combination of electronic or mechanical steering of the sonication volume 222. The lines 216 indicate the rough path of the ultrasound from the ultrasound transducer 210 to the sonication volume 222. From this Fig. it is obvious that if the sonication volume 222 is moved to each of the sonication points 224, 226, 228, 230 that regions of the near field region 217 will be heated more than once. The high-intensity focused ultrasound system 206 is shown as being connected to a hardware interface 242 of computer system 240.

The computer 240 further comprises a processor 244, a user interface 246, computer storage 248, and computer memory 250. The hardware interface 242 enables the processor 244 to send and receive commands and data in order to control the functioning of the medical apparatus 200. The processor 244 is further connected to the user interface 246, the computer storage 248, and the computer memory 250.

The computer storage 248 is shown as containing location data 252. The location data 252 is descriptive of the location of the sonication points 224, 226, 228, 230. The computer storage 248 is further shown as containing a sonication path 254 which has been calculated for each of the sonication points 224, 226, 228, 230. The computer storage 248 is shown as further containing overlap region data 256. The overlap region data 256 contains data of overlaps of the sonication path 254 in the near field region 217. The computer storage 248 is shown as further containing transducer control commands 258. The transducer control commands 258 have been generated to minimize the heating in the near field region 217 when the sonication points 224, 226, 228, 230 are sonicated.

The computer memory 250 is further shown as containing a control module 260. The control module 260 contains computer executable code which enables the processor 244 to control the operation and function of the medical apparatus 200. The computer memory 250 is further shown as containing a geometric transducer element model 262. The geometric transducer element model 262 is able to use the location data 252 to calculate the sonication paths 254. The computer memory 250 is further shown as containing an overlap detection module. The overlap detection module 264 contains computer-executable code which enables the processor 244 to use the sonication path 254 to detect geometrically overlapping regions. The identification of these overlapping regions is 256. The computer memory 250 is further shown as containing transducer control generation module 266. The transducer control generation module 266 is able to use the location data 252 and the overlap region data 256 to generate the transducer control commands 258.

High intensity focused ultrasound (HIFU) is a method to locally heat tissue. While the aim is to heat only a selected target region, surrounding tissue through which the ultrasound travels will inevitably be heated to some extent. Successive sonications with fully or partially overlapping beam path will cause cumulative heating to build up. As a result, cool down periods between sonications are needed to avoid excessive heating in the tissue outside the target region. Long cool down periods can significantly hamper treatment efficiency.

No cool down period between two sonications is needed if the beam paths of the sonications do not overlap. Treatment efficiency can thus be optimized by avoiding overlap between beam paths of different sonications.

Focused ultrasound transducers are typically phased arrays, consist of multiple transducer elements. The ultrasound beam can be shaped by switching off part of the elements or otherwise adjusting the power transmitted from each element. The beam-shaping is typically used for avoiding heating in sensitive tissue.

Embodiments may combine the two above methods: beam shaping is exploited in minimizing the cumulative heating resulting from overlapping beam paths. The cumulative heating can be decreased by decreasing power in the elements from which the transmitted power travels through the overlapping region. The invention allows shorter cool down periods and thus more efficient treatment.

The size of a target region is most often quite limited. Therefore beam overlapping cannot be entirely avoided just by controlling sonication location. With the aid of beam shaping, the effect of the overlap can be further decreased or it can even be completely avoided.

Also, the heating in the beam path may not be homogenous. Varying tissue properties may result in a somewhat higher temperature rise or slower cool down in some part of the beam path. As a result, even a single sonication can result in unwanted tissue damage, unless it is aborted before achieving the desired result in the target region. With beam shaping, it would be possible to decrease the heating in a specific region, allowing the sonication to continue longer. Moreover, if successive sonications were made close to each other, the cool down time would be dominated by the tissue requiring the longest cool down time. In such a case beam shaping could be used to avoid beam overlap specifically within that tissue.

According the first aspect beam shaping can be used to minimize cumulative heating from sonications with overlapping beam paths. This can be achieved either by switching part of the elements completely off so that there is no overlap at all, or by reducing the power in elements from which the transmitted power goes through the overlapping region so that the cumulative heating/energy density is not larger in this region than elsewhere in the beam path.

According to the second aspect, beam shaping can be used to prevent excessive heating locally in regions that are especially prone to heating. Such regions could be determined for example based on acquired temperature data or a-priori knowledge. The temperature data could be taken into account dynamically, i.e. immediately when measured. The approach would then be applicable not only for controlling cumulative heating resulting from multiple sonications, but also for preventing excessive heating during a single sonication.

Figure 3:
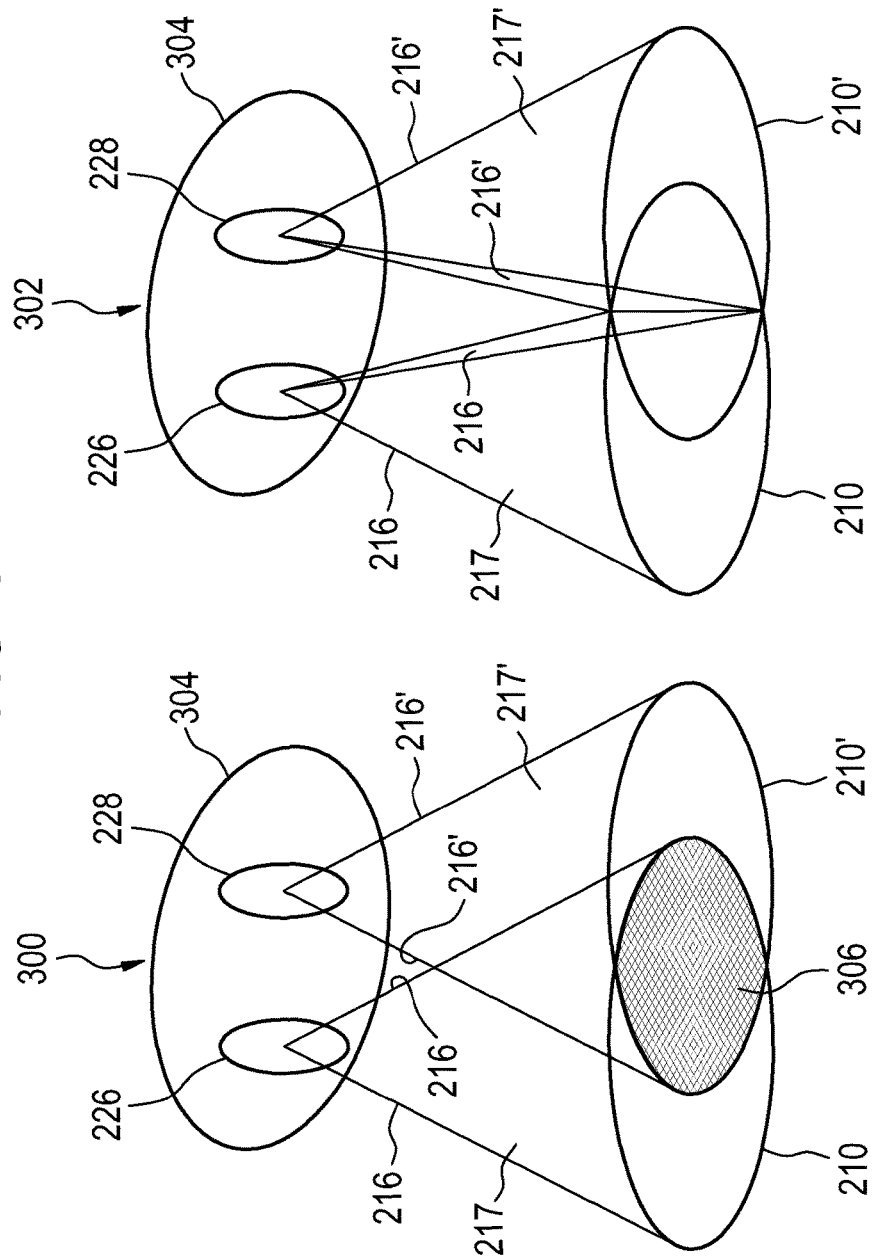
FIG. 3 shows two views of an ultrasonic transducer in a first position and a second position.

FIG. 3 shows two views 300 and 302 of the ultrasound transducer 210, 210'. In view 300 the ultrasound transducer 210 is shown in a first position 210 and a second position 210'. The ultrasound in the two different positions follows a path that was illustrated in FIG. 2. When the ultrasound transducer is in the first position 210 the ultrasound follows the volume defined by the lines 216 and there is a near field region 217. The ultrasound is being focused into the sonication point 226. When the ultrasound transducer is in the second position 210' the volume of ultrasound is defined by the lines 216' and is focused into the sonication point 228. In the second position 210' there is a near field region 217'. The volume defined by the line 304 contains the sonication points 226 and 228. It can be seen that when the transducer is in the first 210 and second positions 210' there is an overlapping region 306 of the two near field regions 217 and 217'. If the sonication points 226 and 228 are sonicated sequentially then the overlapping region 306 will be heated twice. This may lead to thermal damage to the tissue in the overlapping region 306. View 302 shows how an embodiment of the invention may reduce the heating in the overlapping region 306. In this embodiment the active region of the ultrasound transducers 210, 210' is reduced. It can be seen that the volume defined by the lines 216 does not intersect the volume of ultrasound defined by the lines 216'. In this embodiment there is essentially no or very minimal overlap of ultrasound when the two sonication points 226 and 228 are sonicated. This may reduce heating in the near field region 217, 217' and may enable more rapid sonication of the sonication points 226, 228 because there does not need to be as much or a reduced waiting time between the two sonications.

In FIG. 3 the ultrasound beam is represented with a simple geometric model. The element switch off could as well be based on a more sophisticated model of the energy density distribution, such as simulations. Furthermore, local variations in tissue properties can be taken into account for more accurate estimation.

In addition to energy density distribution the method could also be based on simulated or measured temperature distribution or any combination of these. The measured temperature data can be taken into account dynamically, already during an individual sonication, i.e. elements can be switched off in the region where large heating is measured.

In the simplest form, the invention could be used to simply minimize the cool down period needed prior to an individual sonication manipulating the beam shape only for that sonication based on the knowledge about previous sonication. For even more efficient therapy, the entire treatment plan, including following sonications, could be taken into account.

Figure 4:
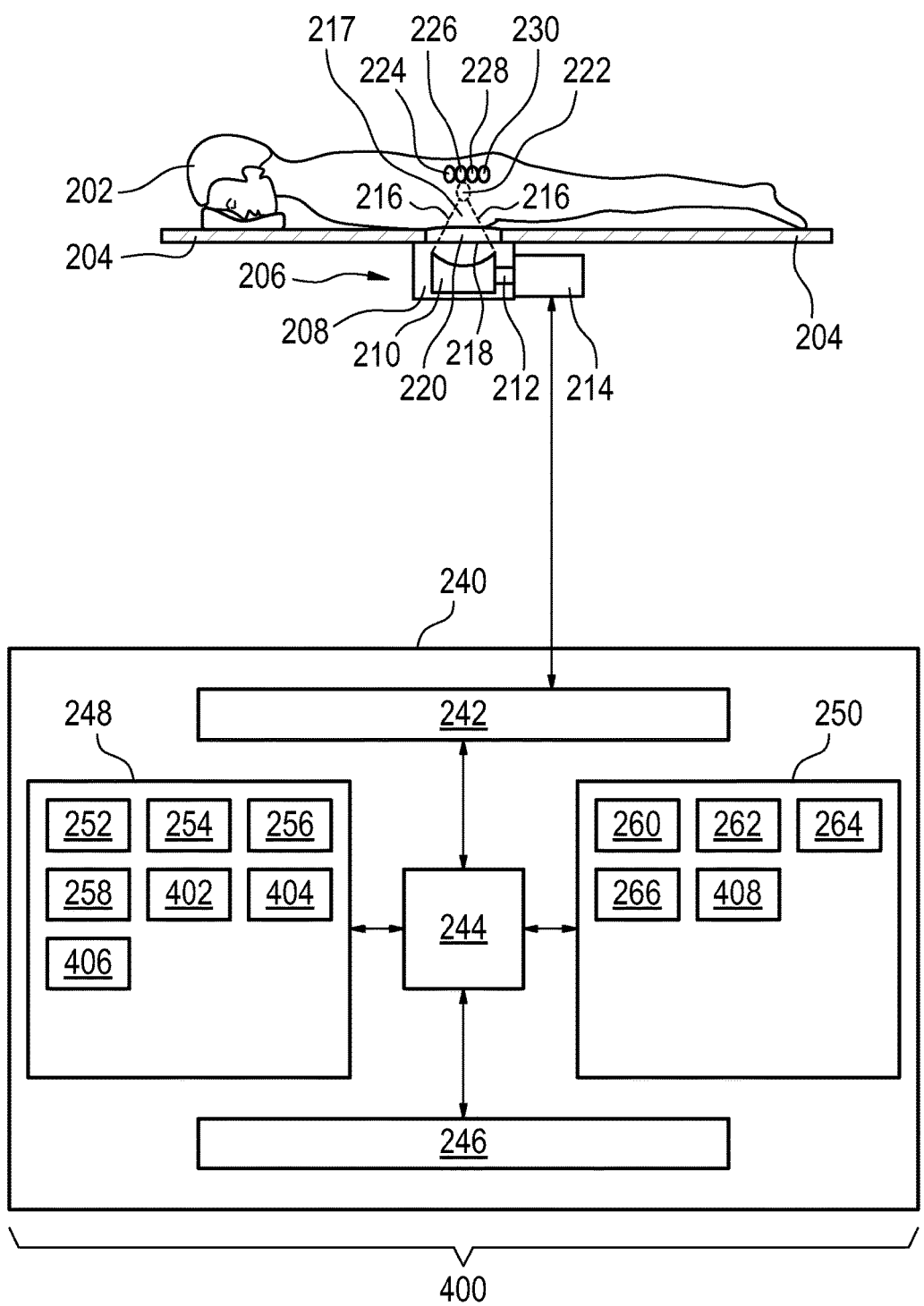
FIG. 4 shows a further example of a medical apparatus.

FIG. 4 shows a medical apparatus 400 according to a further embodiment of the invention. The medical apparatus 400 shown in FIG. 4 is similar to the medical apparatus 200 shown in FIG. 2. The apparatus 400 shown in FIG. 4 has additional software components which modify the functionality of the medical apparatus 400. In this embodiment the computer storage 248 is shown as containing a thermal property map 402. The thermal property map 402 is descriptive of a thermal property in the near field region 217 of the subject 202. The computer storage 248 is further shown as containing a previous thermal dose 404 which is descriptive of a previous thermal dose received by the subject 202. The computer storage 248 is shown as further containing corrected transducer control commands. The corrected transducer control commands were calculated using the previous thermal dose and/or the predicted thermal property map. Not all embodiments will have both the previous thermal dose and the thermal property map 402.

The computer memory is shown as containing a transducer thermal model 408 which is used to calculate the predicted thermal property map 404 from the thermal property map 402 and/or the previous thermal dose 404. The corrected transducer control commands 406 were calculated using the predicted thermal property map 404, the location data 252 and the overlap region data 256 by the transducer control command generation module 266.

Figure 5:
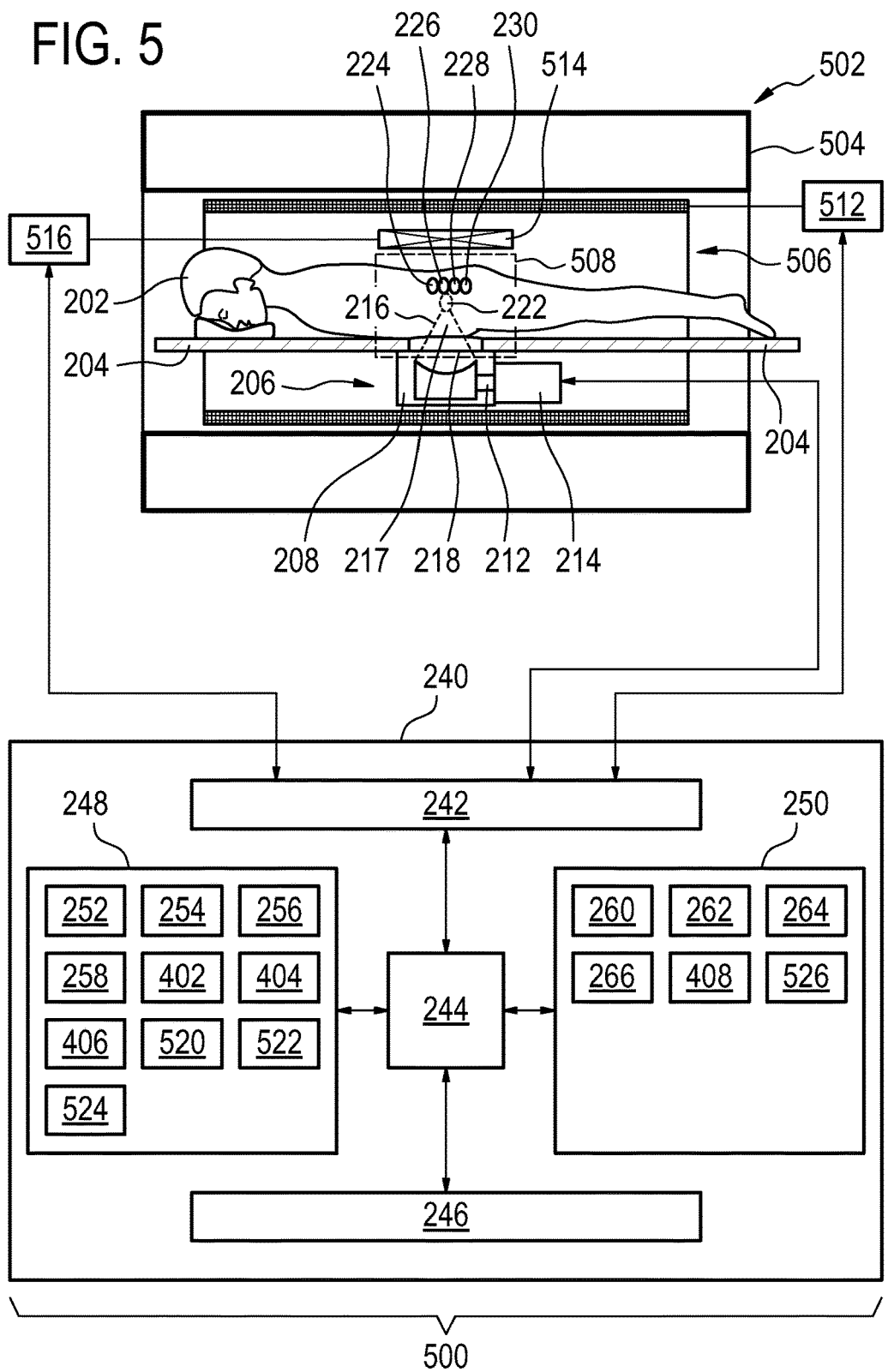
FIG. 5 shows a further example of a medical apparatus.

FIG. 5 shows a further example of a medical apparatus 500. The medical apparatus 500 is similar to the medical apparatuss 400 shown in FIG. 4. In this embodiment there is a magnetic resonance imaging system 502 for acquiring thermal magnetic resonance data. The magnetic resonance imaging system comprises a magnet 504. The magnet 504 is a cylindrical type superconducting magnet with a bore 506 through the center of it. In various embodiments the mechanical actuator/power supply 214 is located outside or inside of the bore 506 of the magnet 504.

The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 506 of the cylindrical magnet there is an imaging zone 508 where the magnetic field is strong and uniform enough to perform magnetic resonance imaging.

Within the bore 506 of the magnet there is also a set of magnetic field gradient coils 510 which are used for acquisition of magnetic resonance data to spatially encode magnetic spins within the imaging zone 508 of the magnet 504. The magnetic field gradient coils are connected to a magnetic field gradient coil power supply 512. The magnetic field gradient coils 510 are intended to be representative. Typically magnetic field gradient coils contain three separate sets of coils for spatially encoding in three orthogonal spatial directions. A magnetic field gradient power supply 512 supplies current to the magnetic field gradient coils 510. The current supplied to the magnetic field coils is controlled as a function of time and may be ramped or pulsed.

Adjacent to the imaging zone 508 is a radio-frequency coil 514 for manipulating the orientations of magnetic spins within the imaging zone 508 and for receiving radio transmissions from spins also within the imaging zone. The radio-frequency coil may contain multiple coil elements. The radio-frequency coil may also be referred to as a channel or an antenna. The radio-frequency coil 514 is connected to a radio frequency transceiver 516. The radio-frequency coil 514 and radio frequency transceiver 516 may be replaced by separate transmit and receive coils and a separate transmitter and receiver. It is understood that the radio-frequency coil 514 and the radio-frequency transceiver 516 are representative. The radio-frequency coil 514 is intended to also represent a dedicated transmit antenna and a dedicated receive antenna. Likewise the transceiver 516 may also represent a separate transmitter and receivers.

The computer storage 248 is shown as containing a pulse sequence 520. A pulse sequence as used herein is a sequence of commands performed at different times which enable a magnetic resonance imaging system 502 to acquire magnetic resonance data 522. The computer storage 248 is shown as containing thermal magnetic resonance data 522 that has been acquired using the magnetic resonance imaging system 502. The computer storage 248 is also shown as containing a thermal property map 524. The thermal property map 524 has been reconstructed from the thermal magnetic resonance data 522.

The computer memory 250 is shown as containing an image reconstruction module 526. The image reconstruction module 526 contains computer-executable code 244 which enables the processor to construct the thermal property map 524 from the thermal magnetic resonance data 522. This embodiment is shown as containing a previous thermal dose 404 in the computer storage 248. The previous thermal dose 404 is optional in this embodiment.

The magnetic resonance imaging system 502 may also be used for guiding the high-intensity focused ultrasound system 206. For instance through normal magnetic resonance imaging the magnetic resonance imaging system 502 may be used to identify anatomical landmarks within the subject 202 to identify the location of the sonication points 224, 226, 228 and 230.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 200 medical apparatus
202 subject
204 subject support
206 high intensity focused ultrasound system
208 fluid filled chamber
210 ultrasound transducer
210' ultrasonic transducer in $2^{nd}$ position
212 mechanism
214 mechanical actuator/power supply
216 path of ultrasound
216' path of ultrasound in $2^{nd}$ position
217 near field region
217' near field region in $2^{nd}$ position
218 ultrasound window
220 gel pad
222 sonication volume
224 sonication point
226 sonication point
228 sonication point
230 sonication point
240 computer system
242 hardware interface
244 processor
246 user interface
248 computer storage
250 computer memory
252 location data
254 sonication path
256 overlap region data
258 transducer control commands
260 control module
262 geometric transducer element model
264 overlap detection module
266 transducer control command generation module
300 first view
302 second view
304 target volume
306 overlapping region in near field
400 medical apparatus
402 thermal property map
404 previous thermal dose
404 predicted thermal property map
406 corrected transducer control commands
408 transducer thermal model
500 medical apparatus
502 magnetic resonance imaging system
504 magnet
506 bore of magnet
508 imaging zone
510 magnetic field gradient coils
512 magnetic field gradient coils power supply
514 radio-frequency coil
516 transceiver
520 pulse sequence
522 thermal magnetic resonance data
524 thermal property map
526 image reconstruction module

The invention claimed is:

1. A medical apparatus comprising:
a high intensity focused ultrasound system comprising an ultrasound transducer with multiple transducer elements for focusing ultrasound into a sonication volume, wherein there is a near field region between the ultrasonic transducer and the sonication volume, wherein the multiple transducer elements are controllable in groups;
a memory for storing machine executable instructions;
a processor for controlling the medical apparatus, wherein execution of the machine executable instructions causes the processor to:
receive location data descriptive of at least first and second sonication points, the second sonication point sequentially following the first sonication point, wherein the ultrasonic transducer is in a first position to focus the ultrasound into the first sonication point and the ultrasonic transducer is in a second position to focus the ultrasound into the second sonication point;

determine, using a geometric model or ray tracing, for each transducer element group, first and second sonication paths based on a respective location of the first and second sonication points;

detect, using the first and second sonication paths, a geometrically-overlapping region of the first and second sonication paths in the near field region;

generate transducer control commands, using the geometrically-overlapping region and the respective location of the first and second sonication points, wherein the transducer control commands are configured to control the multiple transducer elements to reduce deposition of ultrasonic energy in the geometrically-overlapping region during a sonication of the first and second sonication points by any of the following: selectively turning off one or more of the multiple transducer elements, reducing an amplitude of the ultrasonic energy generated by one or more of the multiple transducer elements, and combinations thereof; and control the high intensity focused ultrasound system to sequentially sonicate the first and second sonication points using the transducer control commands, thereby reducing a heating of the near field region to enable a more rapid sonication of the first and second sonication points by reducing a waiting time between the sonication of the first and second sonication points.

2. The medical apparatus of claim 1, wherein execution of the instructions further causes the processor to:
receive a current thermal property map descriptive of a thermal property in the near field region,
calculate a predicted thermal property map of the thermal property using the transducer control commands and a transducer thermal model;
determine corrected transducer control commands using the predicted thermal property map, wherein the corrected transducer control commands are configured to control the multiple transducer elements, wherein the instructions are configured to cause the processor to use the corrected transducer control commands to control the high intensity focused ultrasound system during the sequential sonication of the first and second sonication points.

3. The medical apparatus of claim 2, wherein execution of the instructions further causes the processor to receive a previous thermal dose, wherein the previous thermal dose is descriptive of the thermal dose caused by a previous sonication using the high intensity focused ultrasound system, and wherein the current thermal property map and/or the predicted thermal property map are at least partially determined using the previous thermal dose.

4. The medical apparatus of claim 2, wherein the medical apparatus further comprises a magnetic resonance imaging system for acquiring thermal magnetic resonance data, wherein execution of the instructions further causes the processor to:
acquire the thermal magnetic resonance data, and
calculate the current thermal property map at least partially using the thermal magnetic resonance data.

5. The medical apparatus of claim 2, wherein execution of the instructions causes the processor to calculate the current thermal property map at least partially using the transducer thermal model and a set of previous transducer control commands.

6. The medical apparatus of claim 1, wherein execution of the instructions further causes the processor to repeatedly:
receive a current thermal property map,
calculate a predicted thermal property map using the transducer control commands and a transducer thermal model;
determine corrected transducer control commands using the predicted thermal property map; and
control the high intensity focused ultrasound system to sequentially sonicate the first and second sonication points using the corrected transducer control commands.

7. The medical apparatus of claim 1, wherein each of the multiple transducer element groups are individually controllable.

8. The medical apparatus of claim 2, wherein the thermal property is any one of the following: temperature, maximum temperature, thermal dose, cool down time, and combinations thereof.

9. A non-transitory storage medium storing executable instructions for execution by a processor controlling a medical apparatus, wherein the medical apparatus comprises a high intensity focused ultrasound system comprising an ultrasound transducer with multiple transducer elements for focusing ultrasound into a sonication volume, wherein there is a near field region between the ultrasonic transducer and the sonication volume, wherein the multiple transducer elements are controllable in groups, wherein execution of the executable instructions causes the processor to:
receive location data descriptive of at least first and second sonication points, the second sonication point sequentially following the first sonication point, wherein the ultrasonic transducer is in a first position to focus the ultrasound into the first sonication point and the ultrasound transducer is in a second position to focus the ultrasound into the second sonication point;
determine, using a geometric model or ray tracing, for each transducer element group, first and second sonication paths based on a respective location of the first and second sonication points;
detect, using the first and second sonication paths, a geometrically-overlapping region of the first and second sonication paths in the near field region;
generate transducer control commands using, the geometrically-overlapping region and the respective location of the first and second sonication points, wherein the transducer control commands are configured to control the multiple transducer elements to reduce deposition of ultrasonic energy in the geometrically-overlapping region during a sonication of the first and second sonication points by any of the following: selectively turning off one or more of the multiple transducer elements, reducing an amplitude of the ultrasonic energy generated by one or more of the multiple transducer elements, and combinations thereof; and
control the high intensity focused ultrasound system to sequentially sonicate the first and second sonication points using the transducer control commands, thereby reducing a heating of the near field region to enable a more rapid sonication of the first and second sonication points by reducing a waiting time between the sonication of the first and second sonication points.

10. The non-transitory storage medium of claim 9, wherein execution of the instructions further causes the processor to:
receive a current thermal property map descriptive of a thermal property in the near field region,
calculate a predicted thermal property map of the thermal property using the transducer control commands and a transducer thermal model; and
determine corrected transducer control commands using the predicted thermal property map, wherein the corrected transducer control commands are configured to control the multiple transducer elements, wherein the instructions are configured to cause the processor to use the corrected transducer control commands to control the high intensity focused ultrasound system during the sequential sonication of the first and second sonication points.

11. The non-transitory storage medium of claim 10, wherein execution of the instructions further causes the processor to receive a previous thermal dose, wherein the previous thermal dose is descriptive of the thermal dose caused by a previous sonication using the high intensity focused ultrasound system, and wherein the current thermal property map and/or the predicted thermal property map are at least partially determined using the previous thermal dose.

12. The non-transitory storage medium of claim 10, wherein the medical apparatus further comprises a magnetic resonance imaging system for acquiring thermal magnetic resonance data, wherein execution of the instructions further causes the processor to:
acquire the thermal magnetic resonance data, and
calculate the current thermal property map at least partially using the thermal magnetic resonance data.

13. A method of operating a medical apparatuses, wherein the medical apparatus comprises a high intensity focused ultrasound system comprising an ultrasound transducer with multiple transducer elements for focusing ultrasound into a sonication volume, wherein the ultrasound transducer is configured to generate a near field region between the ultrasonic transducer and the sonication volume, wherein the multiple transducer elements are controllable in groups, wherein the method comprises:
receiving, by a processor, location data descriptive of at least first and second sonication points, the second sonication point sequentially following the first sonication point, wherein the ultrasonic transducer is in a first position to focus the ultrasound into the first sonication point and the ultrasonic transducer is in a second position to focus the ultrasound into the second sonication point;
determining, by the processor, using a geometric model or ray tracing, for each transducer element group, first and second sonication paths based on a respective location of the first and second sonication points;
detecting, by the processor, using the first and second sonication paths, a geometrically-overlapping region of the first and second sonication paths in the near field region;
generating, by the processor, transducer control commands, using the geometrically-overlapping region and the respective location of the first and second sonication points, wherein the transducer control commands are configured to control the multiple transducer elements to reduce deposition of ultrasonic energy in the geometrically-overlapping region during sonication of the first and second sonication points by any of the following: selectively turning off one or more of the multiple transducer elements, reducing an amplitude of the ultrasonic energy generated by one or more of the multiple transducer elements, and combinations thereof; and
controlling the high intensity focused ultrasound system to sequentially sonicate the first and second sonication points using the transducer control commands, thereby reducing a heating of the near field region to enable a more rapid sonication of the first and second sonication points by reducing a waiting time between the sonication of the first and second sonication points.

14. The method of claim 13, further including:
receiving a current thermal property map descriptive of a thermal property in the near field region;
calculating a predicted thermal property map of the thermal property using the transducer control commands and a transducer thermal model;
determining corrected transducer control commands using the predicted thermal property map, wherein the corrected transducer control commands are configured to control the multiple transducer elements; and
using the corrected transducer control commands to control the high intensity focused ultrasound system during the sequential sonication of the first and second sonication points.

15. The method of claim 14, wherein the medical apparatus further comprises a magnetic resonance imaging system for acquiring thermal magnetic resonance data, and the method further includes:
acquiring the thermal magnetic resonance data, and
calculating the current thermal property map at least partially using the thermal magnetic resonance data.

16. The method of claim 13, further including repeatedly:
receiving a current thermal property map;
calculating a predicted thermal property map using the transducer control commands and a transducer thermal model;
determining corrected transducer control commands using the predicted thermal property map; and
controlling the high intensity focused ultrasound system to sequentially sonicate the first and second sonication points using the corrected transducer control commands.

* * * * *